United States Patent [19]

Beede et al.

[11] 4,248,685

[45] Feb. 3, 1981

[54] METHOD FOR MAKING HYDROPHILIC RANDOM INTERPOLYMER COMPOSITIONS

[75] Inventors: Charles H. Beede, East Brunswick, N.J.; Harold L. Waldman, Lewisburg, Pa.; Theodore Blumig, East Brunswick, N.J.

[73] Assignee: Johnson & Johnson, New Brunswick, N.J.

[21] Appl. No.: 907,374

[22] Filed: May 19, 1978

Related U.S. Application Data

[60] Division of Ser. No. 674,471, Apr. 7, 1976, Pat. No. 4,111,922, which is a continuation of Ser. No. 509,207, Sep. 25, 1974, abandoned, which is a continuation-in-part of Ser. No. 270,118, Jul. 10, 1972, abandoned.

[51] Int. Cl.$^3$ .............................. C08F 2/46; C08F 4/30
[52] U.S. Cl. .............................. 204/159.22; 128/155; 162/161; 162/168 N; 162/168 NA; 526/212; 526/217; 526/220; 526/229; 526/303; 526/306
[58] Field of Search ............... 526/212, 229, 303, 306, 526/217, 220; 204/159.22

[56] References Cited

U.S. PATENT DOCUMENTS

| | | | |
|---|---|---|---|
| 2,677,679 | 5/1954 | Barney | 526/312 X |
| 3,324,017 | 6/1967 | Perry | 526/306 X |
| 3,475,363 | 10/1969 | Gander | 260/29.7 R |
| 3,509,113 | 4/1970 | Monagle | 526/303 X |
| 3,661,880 | 5/1972 | Markert | 526/312 X |
| 3,836,512 | 9/1974 | Chu | 526/306 X |
| 4,115,339 | 9/1978 | Restaino | 526/303 X |

*Primary Examiner*—C. A. Henderson
*Attorney, Agent, or Firm*—Irving Newman

[57] ABSTRACT

Hydrocolloidal dispersions of random interpolymer compositions that have a capacity for absorbing water in amounts of from 10 to 125 times their own weight or greater and are also bacteriostatic are prepared by the polymerization in aqueous medium of a mixture of monomers comprising (1) up to about 90% by weight of an ester of an $\alpha,\beta$-olefinically unsaturated carboxylic acid and a monohydric or polyhydric alcohol having a terminal quaternary ammonium group and (2) at least one $\alpha,\beta$-olefinically unsaturated comonomer in the presence of a crosslinking agent comprising a difunctional monomer derived from an $\alpha,\beta$-olefinically unsaturated carboxylic acid. The interpolymer compositions can be used for binding or coating nonwoven fabrics including paper to improve water absorbency, or cast into a structurally self-supporting film. A water dispersion of the interpolymer can also be formed into a gel, which can be shaped into useful articles or alternatively dried and pulverized into bacteriostatic hydrophilic particles.

13 Claims, No Drawings

METHOD FOR MAKING HYDROPHILIC RANDOM INTERPOLYMER COMPOSITIONS

CROSS-REFERENCE TO RELATED APPLICATION

This application is a division of copending application Ser. No. 674,471, filed Apr. 7, 1976, now U.S. Pat. No. 4,111,922 issued Sept. 5, 1978, which application is in turn a continuation of application Ser. No. 509,207, filed Sept. 25, 1974, now abandoned, which application is in turn a continuation-in-part of application Ser. No. 270,118, filed July 10, 1972, now abandoned.

BACKGROUND OF THE INVENTION

1. Field of the Invention

This invention relates to novel compositions which are random interpolymers of a terminally quaternized derivative of acrylic acid with an $\alpha,\beta$-olefinically unsaturated comonomer polymerizable therewith, and to their preparation by polymerization in an aqueous medium. More particularly, this invention relates to hydrophilic interpolymer compositions having novel bacteriostatic properties which, in conjunction with their high water adsorbency, makes them especially suitable for applications where the combination of such water adsorbency with control of bacterial growth is desired.

2. Description of the Prior Art

There has long been a need for polymers which can be prepared by polymerization in aqueous systems and which can be cast as self-supporting films having a large water adsorbent capacity. There has also been a need for such compositions that are bacteriostatic and can therefore control the growth of bacteria on surfaces which they contact. Some polymeric compositions, such as polyvinyl alcohol and cellophane, are excellent film formers yet are unable to adsorb water in appreciable amounts. Other materials, exemplified by the so-called "Hydron" polymers, are more water adsorbent than the above films, but cannot be converted to flexible films from aqueous dispersions. Such materials, if they are to be converted into films, must be polymerized in non-aqueous, organic solvents which are termed "syrups", as disclosed in U.S. Pat. No. 3,520,949. Likewise, these polymers lack bacteriostatic properties. When the above prior art compositions are bacteriostatic, they are rendered so by the inclusion of an additional substance, which is not an integral part of the polymer.

SUMMARY OF THE INVENTION

The present invention provides a random interpolymer that is bacteriostatic, is capable of adsorbing large multiples of its own weight of water, and can be prepared by polymerization in an aqueous polymerization medium. More particularly, the bacteriostatic random interpolymers of this invention exhibit the properties of having a water adsorbing capacity of from about 10 to about 125 times their own weight or greater.

In accordance with one aspect of the invention, the random interpolymers are provided in the form of an aqueous colloidal dispersion or suspension which can be converted into a gel, or a dry powder, which find uses as highly adsorbent thickening agents. In addition, articles can be coated with the interpolymers to give them a lubricious coating such, for example, as medical instruments and devices which are to be inserted into body openings e.g., proctoscopes and the like.

In accordance with another aspect of the invention, the random interpolymers may be prepared initially in the form of a gel. In either event, the gelled material, when in a highly cross-linked form, can be cut and shaped into various structures such as contact lenses where the bacteriostatic properties of the interpolymer material can be advantageously employed.

Further, the aqueous colloidal dispersion can be cast into a self-supporting, transparent, conformable film which is particularly useful as a wound dressing since it is highly conforming to wound surfaces, and provides an occlusive bacteriostatic dressing. As set forth in Hinman, C. D., and Maibach, H. I.: Effect Of Air Exposure and Occlusion On Experimental Human Skin Wounds, Nature 200:377, 1963, and Winter, G. D. & Scales, J. T.: Effect Of Air Drying & Dressings On The Surface Of A Wound, Nature 197:91, 1963, it has been shown that the healing of superficial wounds can be enhanced by providing an occlusive dressing. But under such dressings bacteria often can proliferate. However, dressings prepared from the interpolymers of this invention are not only occlusive, but also, because of their bacteriostatic properties, help prevent the proliferation of bacteria.

In accordance with yet another aspect of this invention, the random interpolymers of the invention are prepared by the polymerization in aqueous medium of (A) a mixture of monomers comprising (1) up to about 90% by weight of an ester of an $\alpha,\beta$-olefinically unsaturated carboxylic acid and a monohydric or polyhydric alcohol having a terminal quaternary ammonium group and (2) at least one $\alpha,\beta$-olefinically unsaturated comonomer, in the presence of (B) a cross-linking agent comprising a difunctional monomer derived from an $\alpha,\beta$-olefinically unsaturated carboxylic acid.

DESCRIPTION OF THE PREFERRED EMBODIMENTS

There has now been discovered a novel composition comprising a random interpolymer derived from the polymerization of a mixture of monomers comprising: (A) (1) from about 10 to about 90% by weight of said mixture of a first monomer which is an ester of an $\alpha,\beta$-olefinically unsaturated carboxylic acid and a monohydric or polyhydric alcohol having a terminal quaternary ammonium group and (2), correspondingly, from about 90 to about 10% by weight of said mixture of at least one $\alpha,\beta$-olefinically unsaturated comonomer capable of being dispersed in aqueous media, in the presence of (B) at least 0.02% by weight, based on the weight of said mixture, of a cross-linking agent comprising a difunctional monomer which is capable of being dispersed or dissolved in aqueous media and is an ester or amide of an $\alpha,\beta$-olefinically unsaturated carboxylic acid; said comonomer (2) comprising (a) at least 10% by weight of said mixture of monomers of an acid comonomer, or (b) at least 20% by weight of said mixture of monomers of an amide comonomer, or (c) at least 10% by weight of said mixture of monomers of a combination of acid and amide comonomers, said combination containing at least 5% by weight of said mixture of an acid monomer.

The esters of an $\alpha,\beta$-olefinically unsaturated carboxylic acid and a monohydric or polyhydric alcohol having a terminal quaternary ammonium group which may be suitably employed in this invention include those having the structure:

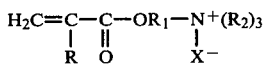

wherein R is selected from the group consisting of hydrogen and $C_1$ to $C_4$ alkyl; $R_1$ is selected from the group consisting of $C_1$ to $C_4$ alkylene and hydroxy substituted $C_1$ to $C_4$ alkylene; each $R_2$ is selected from the group consisting of $C_1$ to $C_4$ alkyl; and $X^-$ represents an anion of an acid sufficiently acidic to form a salt with amino nitrogen, for example $Cl^-$, $Br^-$, $I^-$, and $CH_3SO_4^-$. Such esters are exemplified by 2-methacryloyloxyethyltrimethylammonium methyl sulfate and 2-hydroxy-3-methacryloyloxypropyltrimethylammonium chloride, the latter being preferred.

Difunctional monomers suitable for use as a crosslinking agent in accordance with this invention include the esters and amides of $\alpha,\beta$-olefinically unsaturated acids selected from the group consisting of the compounds defined by structural formulas I, II and III below:

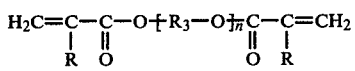

wherein R is hydrogen or $C_1$ to $C_4$ alkyl; $R_3$ is $C_1$ to $C_6$ alkylene; and n is an integer from 1 to 3;

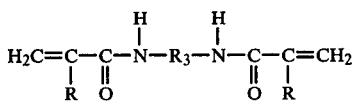

wherein R is hydrogen or $C_1$ to $C_4$ alkyl; and $R_3$ is $C_1$ to $C_6$ alkylene; and

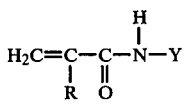

wherein R is hydrogen or $C_1$ to $C_4$ alkyl; and Y is selected from the group consisting of

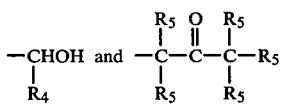

wherein $R_4$ is selected from the group consisting of hydrogen and $C_1$ to $C_5$ alkyl; and each $R_5$ is selected from the group consisting of hydrogen and $-CH_2OH$, provided, however, that at least one $R_5$ is $-CH_2OH$.

Examples of such difunctional monomers include ethylene glycol dimethacrylate and diacrylate, diethyleneglycol dimethacrylate and diacrylate, triethyleneglycol dimethacrylate and diacrylate, 1,3-propanediol dimethacrylate and diacrylate, 2,2-dimethylpropanediol diacrylate, tripropylene glycol dimethacrylate and diacrylate, 1,3-butylene glycol dimethacrylate and diacrylate, N,N'-propylenebisacrylamide, N,N'-methylenebisacrylamide; N-1-alkylol amides of $\alpha,\beta$-olefinically unsaturated carboxylic acid, which amides have from 4 to 8 carbon atoms, exemplified by N-methanol acrylamide, N-1-ethanolacrylamide, N-1-propanolacrylamide, N-methanolmethacrylamide, N-1-ethanolmethacrylamide and hydroxymethyl diacetone acrylamide (available from Lubrizol Corporation). The preferred difunctional monomer is N,N'-methylenebisacrylamide.

The olefinically unsaturated monomers that are suitable for employment as comonomers in the random interpolymers of this invention include $\alpha,\beta$-olefinically unsaturated monomers such as the vinyl monomers, as well as $\alpha,\beta$-olefinically unsaturated carboxylic acids of from 3 to 6 carbon atoms and the lower alkyl esters and amides thereof, 2-($C_1$-$C_4$) alkyl substituted acrylic and crotonic acids and esters and amides thereof, and N-substituted amides of the above acids. Examples of suitable $\alpha,\beta$-olefinically unsaturated monomers include sodium vinyl sulfate, vinyl acetate, methyl vinyl ether, vinyl chloride, crotonic acid, crotonamide, acrylic acid, methyl acrylate, methyl crotonate, ethyl acrylate, ethyl crotonate, methacrylic acid, 2-ethylacrylic acid, 2-methylcrotonic acid, butyl methacrylate, ethyl methacrylate, ethyl 2-methylcrotonate, acrylamide, methacrylamide, 2-ethylcrotonamide, 2-ethylacrylamide, N-isopropyl acrylamide, diacetone acrylamide, N-t-butyl acrylamide, N-2-ethanol acrylamide, N-3-propanol acrylamide and N-methyl methacrylamide. Of these, the preferred comonomers are acrylic and methacrylic acids, acrylamide and methacrylamide.

In a preferred embodiment of this invention, the mixture of monomers comprises from about 10 to about 80% by weight of said mixture of said $\alpha,\beta$-olefinically unsaturated carboxylic acid ester of a monohydric or polyhydric alcohol having a terminal quaternary ammonium group; and at least about 20% by weight of the mixture of an olefinically unsaturated comonomer, from about 5 to about 35% by weight of the mixture (total monomers in the prepolymer blend-excluding the crosslinking agent) comprising a comonomer selected from the group consisting of acrylic acid and methacrylic acid (acrylic acid being most preferred), and from about 10 to about 85% by weight of the mixture comprising acrylamide, or methacrylamide (acrylamide being most preferred). Clearly the total amount of the monomers employed will be 100% and therefore if an amount equal to or approaching the maximum of one particular monomer is employed, then the relative amounts of the remaining monomers must be reduced accordingly. The amount of difunctional monomer crosslinking agent employed in this preferred embodiment is from about 0.02 to about 5%, based on the weight of the mixture, from about 0.05 to about 1% being particularly preferred. Generally, when the intended end use of the random interpolymer is as a film, the amount of crosslinking agent will not exceed 0.5% although this may vary depending on the particular crosslinking agent, as well as the composition of the monomer mixture. The selection of a suitable concentration of crosslinking agent (as well as monomer mixture) to meet a particular end use requirement is, however, well within the skill of the art.

The random interpolymers of this invention are prepared, in accordance with another embodiment of this invention, by the free radical polymerization of the above monomers in an aqueous medium using any suitable free radical initiator, including high energy irradiation as well as photochemical and chemical means.

Suitable chemical initiators are any of those which are commonly known in the art to effect the polymerization of acrylic monomers and which are dispersible or soluble in aqueous medium. Such initiators are capable of generating a sufficient number of free radicals to propagate the polymerization reaction, and include water soluble persulfated salts such as sodium, potassium, and ammonium persulfate; t-butyl peroxypivalate; the peroxycarbonate salts; hydrogen peroxide; and water soluble oxidation and reduction couples such as the combination of a water soluble persulfate and a water soluble bisulfite.

In particular, there is preferred the use of the water soluble persulfates, especially ammonium persulfate, and such "redox" pairs as those comprising water soluble persulfates as the oxidant and ammonium bisulfite as the reductant.

These initiators are typically employed in a quantity ranging from about 0.2 to about 2 parts by weight per hundred parts of total monomers (phm). The preferred initiators and especially ammonium persulfate are employed in amounts of from 0.5 to 1 phm.

As used herein, the term "aqueous medium" is meant to include water as well as a fluid comprising water and one or more water-miscible organic solvents. In general, the aqueous medium may comprise water alone, especially deionized water, and may further comprise, in instances where it is desirable to increase the tolerance of the aqueous medium for various monomers otherwise poorly dispersible in water at their higher levels within the foregoing description so as to achieve homogeneous polymerization, a water-miscible solvent, e.g. methanol, ethanol, isopropanol, N,N-dimethylformamide, N,N-dimethylacetamide and acetonitrile. The amount of this included organic solvent can be from 0 to about 60% by weight, based on the weight of the aqueous medium, and, in preferred embodiments, is from 0 to about 15% by weight.

The amount of aqueous medium employed should be sufficient to achieve a uniform solution of the monomers. Generally, this amount of aqueous medium will be in the range of 9 to 20 times by weight of aqueous medium based on the total weight of the monomers. In general, if larger quantities of aqueous medium are employed, the polymerization reaction proceeds less rapidly, and there is the further disadvantage of having an additional quantity of aqueous medium which must eventually be removed.

Generally, the order of addition is immaterial when admixing the monomers and aqueous medium. However, in those instances where a monomer is insoluble or poorly soluble in water and is only sparingly soluble in the aqueous medium, such monomer is preferably first dissolved in the water-miscible organic solvent and the resulting solution is then added to the aqueous medium.

In general, the temperature at which the polymerization is carried out is limited only by the stirrability of the reaction mixture. Thus, at too high a reaction temperature, the viscosity of the reaction mixture rapidly increases to a point where the reaction mixture is too viscous to be stirred and the reaction is then difficult to control and must be terminated. The polymerization rate, however, depends both upon the polymerization initiator employed and the temperature at which the reaction is run.

In the preferred embodiment of this invention in which ammonium persulfate is used as the initiator, the reaction is suitably conducted at a temperature range of about 55° to 75° C. Preferably, when less than 60% by weight of the monomer mixture is a terminally quaternized monomer, the reaction temperature should not exceed about 68° C. It is also preferred that the time at the elevated temperature be limited to about 20 to 45 minutes, so as to limit the viscosity of the reaction mixture (at the reaction temperature) to no more than about 3,000 centipoise. After the reaction has proceeded for this period, it is preferred to rapidly cool the reaction mixture to below 30° C. It has been found that when the duration at elevated temperature is thus limited, a random interpolymer is produced that will remain as a stable (uniform) hydrocolloidal dispersion, having a viscosity at 25° C. of from about 40 to about 10,000 centipoise, for a period of from 1 to 24 months or longer at room temperature.

Once the polymerization reaction has proceeded to the point where the random interpolymerized product exists as a gel rather than a hydrocolloidal dispersion, smooth films can no longer be cast. After the hydrocolloidal dispersion has formed a gel, the gelled random interpolymer may be dried and pulverized into a powder. In this powder form, it does retain its highly hydrophilic and bacteriostatic properties, but cannot be readily redispersed in water as a colloidal dispersion.

Of course, a dry product or a gel may be preferred for various applications. In such instances the hydrocolloidal dispersion of random interpolymer can be converted into a gel by storing at elevated temperatures, e.g. 30°–40° C., for from one to eight weeks. If desired, this gel can be used as is or dried and pulverized into a powder as discussed above. Alternatively, the hydrocolloidal dispersion can be dried directly by well-known means, for example drum drying or spray drying, to form substantially dry hydrophilic particles of the interpolymer.

In a less preferred alternative method, the interpolymers can be prepared by the quaternization of corresponding interpolymers prepared with monomer having the free amino group instead of the quaternary monomer, using well-known techniques. One disadvantage of this procedure, particularly for medical or other end uses where the ultimate product may contact people or animals, is that incomplete quaternization may leave some free amino groups in the end product, and these tend to be irritating and cause undesirable side effects.

The interpolymers of this invention are useful in the form of a hydrocolloidal dispersion, as a film, as a gel and in the form of particles prepared by the pulverization of the dried interpolymer. The particulate form can be used as a thickening agent in the so-called "water base" paints, or interspersed within a fibrous material, for example, paper products or other woven or nonwoven fabric materials (used, for example, as towels, disposable diapers and the like) where its combination of water adsorbency and antibacterial properties can be employed to special advantage. The hydrocolloidal dispersion itself can be used per se in impregnating and coating operations for direct application to an article. Examples of such uses include the application of a hydrophilic lubricious coating to a medical instrument that is intended for insertion into a body opening such, for example, as a disposable rectal thermometer, or to the surfaces of latex gloves used by physicians in carrying out physical examinations of such body cavities.

The interpolymers are especially useful when cast into a tough, integral film. As a film, the interpolymers are particularly well-suited for covering minor wounds such as cuts, scratches, and other irritated skin areas where a dressing is indicated.

The interpolymers have been shown to have in vitro bacteriostatic properties, and in vivo studies on intact skin have also established such activity. Thus, the cast films prepared from these interpolymers are well-suited as occlusive dressings for minor wounds such as cuts, scratches, and irritated areas.

To cast a film of the interpolymer of this invention, an aqueous dispersion of the interpolymer, preferably a dispersion of the interpolymer in the aqueous polymerization medium, is disposed on a smooth, non-adherent surface such as polyethylene, polytetrafluoroethylene or silicone-treated surfaces.

The films can be cast in a variety of thicknesses. The details for film casting are well-known in the art, and such well-known procedures can be advantageously employed in preparing the interpolymer films of this invention. When a film is to be prepared from the interpolymers of this invention, increased film flexibility can be achieved by including in the polymeric dispersion prior to casting from 5 to 40% by weight of a plasticizer such for example as glycerol, carbitol or methyl carbitol, glycerol being preferred.

The following examples will further serve to illustrate the preparation and use of the interpolymers of this invention.

EXAMPLE I

A 5-liter multi-neck flask, equipped with a nitrogen inlet, mechanical stirrer, thermometer, reflux condenser and an addition funnel was charged with the following reagents:

| | |
|---|---|
| 2-hydroxy-3-methacryloyloxypropyl-trimethylammonium chloride, Sipomer Q-1, Alcolac Chemical Corporation | 108 g. |
| Acrylic acid | 24 g. |
| Acrylamide | 108 g. |
| N,N′-methylenebisacrylamide | 0.12 g. |
| Water | 2700 g. |

After purging the system with nitrogen for 100 minutes, the contents were heated until the temperature reached 55° C. Then a solution of ammonium persulfate, (2.4 g.) in 10 ml. of water was added. When the temperature reached 68°, and the viscosity of the reaction mixture became such that the stirrer began to labor, then 240.0 g. of methanol were added over a 10 min. period and the reaction mixture cooled. The colloidal dispersion obtained had a solids content of 7.76%, equivalent to 100% conversion. A film is obtained by drying down, in a polyethylene lined tray having a surface area of about 40 $cm^2$ and containing a piece of gauze or similar fabric to act as a reinforcement, 200 g. of the above dispersion to which is added 5 g. of glycerol, at 100° F. for 48 hours. A weighed sample of the film is placed in 150 g. of deionized water for 24 hours. The mixture is then strained through 40 mesh screening.

EXAMPLE II

A 5-liter, multi-necked flask, equipped with a nitrogen inlet, mechanical stirrer, thermometer and reflux condenser was charged with the following reagents:

| | |
|---|---|
| 2-hydroxy-3-methacryloyloxypropyl-trimethylammonium chloride | 126 g. |
| Acrylamide | 126 g. |
| N,N′-Methylenebisacrylamide | 0.14 g. |
| Acrylic acid | 28 g. |
| Methanol | 280 g. |
| Water | 3175 g. |

The system was purged with nitrogen for approximately 60 minutes. The reaction mixture was then heated until the temperature reached 55° C. At this time a solution of 1.4 g. of ammonium persulfate in 25 ml. of water was added. When the temperature reached 63.5° C., heating was discontinued, and the temperature ws maintained between 63° and 64° C. for 10 minutes. The reaction mixture was cooled to 24.5° C. and filtered air was bubbled through the stirred reaction mixture for 2 hours. The colloidal dispersion so obtained had a solids content of 7.37% and a viscosity of 80 cP. A film was obtained by drying down, in a polyethylene lined tray having a surface area of about 40 $cm^2$, and containing a piece of gauze or similar fabric to act as a reinforcement, 200 g. of the above dispersion to which added 5 g. of glycerol, at 100° F. for 48 hours. A weighed sample of the film was placed in 150 g. of deionized water for 24 hours. The mixture was then strained through 40 mesh screening and the amount of water adsorbed calculated. For this polymer there was adsorbed 35.5 g. of $H_2O$ per g. of hydrocolloid.

EXAMPLE III

Using the polymerization procedure described in Example I or II, the monomers listed in the following table were polymerized under the conditions and with the results indicated to give colloidal dispersions of interpolymers in accordance with the present invention. The amount of ingredients in the table is in grams.

EXAMPLE III TABLE

| Polymer | A | B | C | D | E | F | G | H | I | J | K | L | M |
|---|---|---|---|---|---|---|---|---|---|---|---|---|---|
| Acrylamide | 54 | 126 | 54 | 126 | 54 | 12 | 63 | 63 | — | — | 63 | 70 | 63 |
| Acrylic Acid | 12 | 28 | — | 28 | 12 | 12 | 14 | 14 | 35 | 42 | 14 | — | 14 |
| DAA[a] | — | — | — | — | — | — | — | — | — | 56 | — | — | — |
| Hydroxyethyl Acrylate | — | — | — | — | — | — | 21 | — | — | — | — | — | — |
| Methacrylamide | — | — | — | — | — | 36 | — | — | — | — | — | — | — |
| N,N′-Methylenebis-acrylamide | .06 | 0.14 | .06 | 0.14 | — | 0.06 | 0.07 | 0.07 | 0.07 | 0.07 | — | 0.07 | 0.07 |
| N-Methylolacrylamide | — | — | — | — | — | — | — | — | — | 1 | — | — | — |
| Sipomer Q-1[b] | 54 | — | 54 | 126 | 54 | 60 | 42 | 63 | 105 | 42 | 63 | 70 | 49 |
| Sipomer Q-5[c] | — | 126 | — | — | — | — | — | — | — | — | — | — | — |
| TEGDM[d] | — | — | — | — | 0.06 | — | — | — | — | — | — | — | — |
| Methacrylic Acid | — | — | 12 | — | — | — | — | — | — | — | — | — | — |
| Methyl Acrylate | — | — | — | — | — | — | — | — | — | — | — | — | 14 |
| Ammonium Persulfate | — | 1.4 | 1.2 | 2.8 | 1.2 | 1.2 | 1.4 | 0.7 | 0.7 | 0.7 | 0.7 | 0.7 | 0.7 |
| Lupersol 11[e] | 3 | — | — | — | — | — | — | — | — | — | — | — | — |
| Water | 1360 | 3300 | 1385 | 3430 | 1375 | 1375 | 1725 | 705 | 1575 | 1600 | 1600 | 1600 | 1600 |
| Methanol | 120 | 280 | 120 | 280 | 120 | 120 | — | 1020 | 140 | 140 | 140 | 140 | 140 |

EXAMPLE III TABLE-continued

| Polymer | A | B | C | D | E | F | G | H | I | J | K | L | M |
|---|---|---|---|---|---|---|---|---|---|---|---|---|---|
| Trisodium phosphate | — | — | — | — | — | — | — | 1.4 | 1.4 | 1.4 | — | — | — |
| Polym. Temp., °C. | 24–51 | 55–64 | 55–64 | 55–64 | 55–64 | 55–64 | 55–65 | 55–63.5 | 55–64.5 | 55–64.5 | 55–64 | 55–64 | 55–65.3 |
| Procedure of Example | I | I | I | I | I | I | g | II | II | II | II | II | II |
| % Solids | 7.8 | 7 | 7.1 | 7 | 6.9 | 7.3 | 7.6 | 8.2 | 7.3 | 6.9 | 7.4 | 7.7 | 7.2 |
| Viscosity, cP. | N.D.[f] | 100 | 113 | 1810 | 380 | 40 | 1310 | 10 | 25 | 30 | 90 | 140 | 100 |
| Absorption Cap. g.H$_2$O/g.HC | 163 | 89 | 88 | 79 | 47 | 75 | 94 | 49 | 52 | 16 | 25 | 34 | 36 |

[a]DAA = diacetone acrylamide - Lubrizol Corp.
[b]Sipomer Q-1 = 2-hydroxy-3-methacryloyloxypropyltrimethylammonium chloride - Alcolac Chemical Corp.
[c]Sipomer Q-5 = 2-methacryloyloxyethyldimethylammonium methyl sulfate - Alcolac Chemical Corp.
[d]TEGDM = Triethyleneglycol dimethacrylate
[e]Lupersol 11 = 75% solution of t-butyl peroxypivalate in mineral spirits
[f]N.D. = Not determined
[g]No methanol was used in this run. As the only essential difference between the procedures of Examples I and II is the point of addition of the methanol, run G procedure cannot be distinguished as between Examples I and II.

EXAMPLE IV

An aqueous dispersion of the interpolymer prepared from 12 g. of acrylic acid, 54 g. of acrylamide, 0.06 g. of N,N'-methylenebisacrylamide and 54 g. of 2-hydroxy-3-methacryloyloxypropyltrimethylammonium chloride in 1520 g. of water and 120 g. of methanol was prepared using 1.2 g. ammonium persulfate as the initiator. The polymerization was carried out at 55° to 63° C. for 0.8 hours. The resulting hydrocolloidal dispersion had a solids content of 6.4% and a viscosity of 193 cP. 4.3 g. of glycerol plasticizer were added to 200 g. of the dispersion and the interpolymer cast as films having thicknesses in the range 20 to 30 mils.

From these films hydrocolloidal film dressings were prepared in the following manner. A 3×3 inch, 1/16 inch thick polyester urethane foam was coated on one side thereof with a pressure sensitive adhesive. A 2¼×2¼ inch portion of the film prepared as described above was affixed to the center area of the coated side of the foam by means of the pressure sensitive adhesive, leaving a ⅜ inch border about the perimeter of the foam to serve as a means for attaching the hydrocolloidal film dressing to the desired skin area.

EXAMPLE V

To illustrate the in vitro bacteriostatic properties of the hydrocolloid film against specific organisms, 2 cm × 2 cm portions of a film of Example IV, without any foam backing, were placed in the center of test plates containing a 10 ml base layer of nutrient agar overlaid with 4 ml agar containing approximately 2,000,000 viable cells of test organism per ml. The plates were then incubated for 24 hours at 32° C. The average zone of inhibition of triplicate trials is set forth below.

Staph. aureus: 2.3 mm (from the edge of the dressing)
Staph. epidermidis: 3 mm (from the edge of the dressing)

Similar activity can be demonstrated against Ps aeroginosa, K. pneumoniae, and E. coli for films produced with 2-hydroxy-3-methacryloyloxypropyltrimethylammonium chloride.

EXAMPLE VI

Hydrocolloid film dressings of Example IV were attached to a human subject's skin and occluded with Saran film. After 48 hours the dressings were removed, and a sample taken by washing the treated area with 1.5 milliliters of physiological saline in a 28 millimeter diameter cylinder. The area was gently scraped for 30 seconds with a sterile pipette. One milliliter of the wash solution was transferred to a tube containing 9 milliliters of peptone water. These suspensions, and dilutions made from them, were plated in Brain Heart Infusion Agar. After incubation for 48 hours, colonies on the plates were counted and the numbers of bacteria per square centimeter of skin calculated.

As shown in the Table below, the dressings of this invention inhibited bacterial growth on intact skin of all of 10 subjects.

TABLE

Bacteria per cm$^2$ recovered from treated and control sites

| Subject | Saran Film Occluded Hydrocolloid Film Dressing | Saran Film Occluded *Dialyzed Hydrocolloid Film Dressing | Saran Film Control | Skin Control |
|---|---|---|---|---|
| 1 | 46 × 10$^2$ | 79 × 10$^3$ | 14 × 10$^5$ | 19 × 10$^2$ |
| 2 | 13 × 10$^2$ | 62 | 50 × 10$^5$ | 22 |
| 3 | >13 | 8 | 22 × 10$^5$ | 17 |
| 4 | >13 | 802 | 21 × 10$^5$ | 74 |
| 5 | 768 | 29 × 10$^2$ | 34 × 10$^4$ | 43 |
| 6 | 142 | 24 | 97 × 10$^4$ | 149 |
| 7 | 89 | 12 | 84 × 10$^4$ | 14 |
| 8 | 5 | 29 × 10$^2$ | 34 × 10$^5$ | 106 |
| 9 | 17 × 10$^3$ | 74 × 10$^2$ | 48 × 10$^4$ | 36 |
| 10 | 18 × 10$^2$ | 46 × 10$^2$ | 31 × 10$^4$ | 70 |

*Dialyzed hydrocolloid film was cast from hydrocolloid dispersion that had been subjected to dialysis to remove any impurities (e.g. unreacted monomer) that may have been present.

EXAMPLE VII

The volar aspect of the left forearm of a human volunteer was shaved and then prepped with a 70% ethanol swab. Three superficial incisions 15 mm. long and approximately 300 microns deep were made with a sterile scalpel (blade No. 11).

The incisions were then dressed with sterile hydrocolloid film with foam backing described in Example IV. The control portions of the wounds were biopsied once to yield information at 1, 2 and 3 days post wounding. The biopsies are small, elliptical samples obtained after infiltration of these areas with ca. 0.3–0.4 cc of 2% lidocaine hydrochloride. The fresh tissue ws quick-frozen for cryotomy (Slee HR Cryostat). Eight micron thick sections were cut, fixed in Wolman's solution and stained with hematoxylin and eosin.

Gross observations of the incisions reveal that a moderate scab formation is present on day 1 and this decreases slightly by the third day. There is no apparent infection, hemorrhage, edema or excessive tenderness. A slight amount of dried serosanquinous exudate is present on the film when removed from the wound.

From the standpoint of histology, day 1 reveals slight inflammation and the wound ws re-epithelialized. A fibrin network is present below the hyperplastic epidermis. Differentiation of the epidermis starts at that time.

By day 2, a slight perivascular inflammatory response is seen in a re-epithelialized wound. A few fibroblasts can be seen in the perivascular areas. The epidermis has a hyperplastic appearance and is differentiated. A few necrotic cells are present in the lifting scab. A dermal fibrin network is present.

By the third day a moderate polymorphonuclear inflammatory response is seen. The wound, as before, is re-epithelialized and hyperplastic. No fibroplasia are noticed. A fibrin network is seen in the dermis and the stratum granulosum is present. A lifting scab is seen and contains only a few necrotic cells.

These studies reveal a well-healed wound by day 2. This is equivalent to saran dressed wounds of the same age. In addition to preventing free evaporation from wound tissues, the foam hydrocolloid dressing probably stabilizes the wound mechanically, i.e., reducing shear forces. This might also be the reason the wound is re-epithelialized and differentiated by day 2. No evidence of any primary irritation or damage to tissue is observed.

EXAMPLE VIII

Cantharidin induced blister wounds were dressed with (a) a sample of hydrocolloid film as prepared in Example IV, (b) another sample of the same hydrocolloid film occluded with Saran film and (c) a Saran film occluded control. The Saran film dressings were affixed by means of surgical tape. After the dressings were in place for 48 hours, the wounds, together with a skin control, were sampled for bacterial growth. Sampling was done by washing the treated area with 2.5 milliliters physiological saline in a 12.7 mm. diameter cylinder. The area was not scraped as with intact skin. Saline was agitated in the cylinder by swishing a pipette back and forth for 60 seconds. One ml. of the wash solution was then transferred to a tube containing 9 ml. of peptone water. These suspensions and dilutions made from them were plated in Brain Heart Infusion Agar. After incubation for 48 hours, colonies on the plates were counted and the numbers of bacteria per square centimeter of skin calculated.

The following Table shows the numbers of bacteria cultured from the blister wounds.

TABLE

| Subject | Hydrocolloid Film | Hydrocolloid Film Occluded | SARAN$^R$ Control | Skin Control |
|---|---|---|---|---|
| 1 | $23 \times 10^6$ | 58 | $94 \times 10^5$ | $35 \times 10^2$ |
| 2 | 23 | 23 | $89 \times 10^4$ | 35 |
| 3 | $10 \times 10^7$ | $37 \times 10^6$ | $62 \times 10^4$ | 173 |
| 4 | 115 | 35 | $37 \times 10^5$ | 104 |
| 5 | 104 | $17 \times 10^3$ | $39 \times 10^5$ | — |
| 6 | 299 | 23 | $11 \times 10^6$ | — |
| 7 | 391 | 12 | $16 \times 10^6$ | $37 \times 10^3$ |
| 8 | $39 \times 10^6$ | 23 | $15 \times 10^6$ | $35 \times 10^2$ |
| 9 | $50 \times 10^6$ | $34 \times 10^6$ | $15 \times 10^6$ | 460 |
| 10 | $11 \times 10^6$ | $11 \times 10^6$ | $12 \times 10^6$ | $24 \times 10^2$ |

EXAMPLE IX

A 3-liter, multinecked flask, equipped with a nitrogen inlet, mechanical stirrer, thermometer and reflux condenser was charged with the following reagents:

| | |
|---|---|
| 2-Hydroxy-3-methacryloyloxypropyl-trimethylammonium chloride | 135 g. |
| Acrylamide | 7.5 g. |
| Acrylic acid | 7.5 g. |
| N,N'-Methylenebisacrylamide | 0.075 g. |
| Water | 1775 g. |

The system was purged with nitrogen for approximately 60 minutes. The reaction mixture was then heated until the temperature reached 55° C. At this time, a solution of ammonium persulfate (0.75 g.) in 25 ml. of water was added and heating continued. Heating was discontinued when the temperature reached 65° C.; and the temperature was maintained between 62° and 66° C. for 30 minutes. The reaction mixture was then cooled rapidly to below 30° C. and filtered air then bubbled through the reaction mixture for 1–2 hours. The colloidal dispersion so obtained had a solids content of 7.7% and a viscosity of 140 cP. A sample of the dispersion was dried in a convection oven at 100° C. for 3 hours, yielding 0.6763 g. of polymer. The dried polymer was then immersed in 150 g. of distilled water for 24 hrs. The mixture was strained through 40 mesh screening and the amount of water absorbed by the polymer calculated. This interpolymer absorbed 40 g. of water per gram of polymer. When another sample was dried at 100° F. for 48 hours, the interpolymer showed no water absorption. When the drying was performed at 100° C. for 19 hours, the water absorption was 8 g. of water per g. of polymer.

EXAMPLE X

Using the polymerization procedure described in Example IX, the monomers listed in the following table were polymerized, dried and tested under the conditions and with the results set forth in the following table. From the drying and water retention data set forth therein, it can be seen that for certain interpolymers within the scope of the present invention, proper selection of drying conditions may be necessary to achieve the desired water retention properties. The amount of ingredients in the table is in grams.

EXAMPLE X TABLE

| Polymer | A | B | C | D |
|---|---|---|---|---|
| Acrylamide | — | 30 | 126 | 120 |
| Acrylic Acid | 10 | — | 28 | 30 |
| Sipomer Q-1[1] | 90 | 120 | 126 | 150 |
| N,N'-Methylenebis-acrylamide | 0.05 | 0.075 | 0.14 | 0.06 |
| Ammonium persulfate | 0.5 | 0.75 | 1.4 | 1.5 |
| Water | 1200 | 1800 | 3025 | 3600 |
| Polymerization Temp. °C. | 55–66 | 55–66 | 55–65 | 55–65 |
| % Solids | 7.7 | 7.8 | 8.3 | 7.6 |
| Viscosity, cP | 70 | 265 | 120 | 375 |
| Absorption, g.H$_2$O/g Polymer | | | | |
| a. Sample dried at 100° F. | N.R.[2] | N.R.[2] | 32.4 | 21.1 |
| b. Sample dried at 100° C., 3 hr. | 84.9 | 18.3 | 36.6 | 35.1 |
| c. Sample dried at 100° C., 19 hr. | 67.3 | 134.6 | 13.4 | 27.8 |

[1]Sipomer Q-1 = 2-hydroxy-3-methacryloyloxypropyltrimethylammonium chloride - Alcolac Chemical Corp.
[2]N.R. = no water retention Now, having described the novel interpolymers of this invention, together with their preparation and use, those skilled in the art will have no difficulty in making changes and modifications which do not depart from the scope or spirit of the invention.

What is claimed is:

1. A process for preparing a random interpolymer derived from the polymerization of a mixture of monomers, said interpolymer having a water adsorbing capacity of at least about 10 times its own weight after having been dried at a temperature of about 100° C. for about 3 hours; this process comprising the steps of (1) selecting said mixture of monomers so that it comprises: (A) from about 10 to about 90% by weight of said mixture of a first monomer which is an ester of an $\alpha,\beta$-olefinically unsaturated carboxylic acid and a monohydric or polyhydric alcohol having a terminal quaternary ammonium group and (B), correspondingly, from about 90 to about 10% by weight of said mixture of at least one $\alpha,\beta$-olefinically unsaturated comonomer capable of being dispersed in aqueous media, said comonomer (B) comprising (1) at least 10% by weight of said mixture of monomers of an acid comonomer, or (2) at least 20% by weight of said mixture of monomers of an amide comonomer, or (3) at least 10% by weight of said mixture of monomers of a combination of acid and amide comonomers, said combination containing at least 5% by weight of said mixture of an acid monomer; (II) distributing said mixture of monomers in from about 9 to about 20 parts by weight of an aqueous medium per part of total monomers, said aqueous medium comprising at least 40% by weight of water and up to about 60% by weight of a water miscible organic solvent, and then (III) initiating said polymerization by means of a free radical initiator selected from the group consisting of high energy radiation, photochemical free radical initiators and chemical free radical initiators that are dispersible or soluble in said aqueous medium in the presence of (IV) at least 0.02% by weight, based on the weight of said mixture, of a cross-linking agent comprising a difunctional monomer which is capable of being dispersed or dissolved in said aqueous medium and is an ester or amide of an $\alpha,\beta$-olefinically unsaturated carboxylic acid.

2. The process of claim 1 in which said first monomer is an ester selected from the group consisting of the compounds having the structural formula:

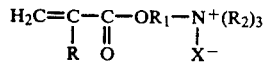

wherein R is selected from the group consisting of hydrogen and $C_1$ to $C_4$ alkyl; $R_1$ is selected from the group consisting of $C_1$ to $C_4$ alkylene and hydroxy substituted $C_1$ to $C_4$ alkylene; each $R_2$ is selected from the group consisting of $C_1$ to $C_4$ alkyl; and $X^-$ represents an anion of an acid sufficiently acidic to form a salt with amino nitrogen.

3. The process of claim 2 in which the ester is 2-methylacryloyloxyethyltrimethylammonium methyl sulfate, or 2-hydroxy-3-methacryloyloxypropyltrimethylammonium chloride.

4. The process of claim 1 in which said comonomer is selected from the group consisting of the vinyl monomers, the $\alpha,\beta$-olefinically unsaturated carboxylic acids of from 3 to 6 carbon atoms and the lower alkyl esters and amides thereof, 2-($C_1$-$C_4$) alkyl substituted acrylic and crotonic acids and esters and amides thereof, and N-substituted amides of the above acids.

5. The process of claim 4 in which said comonomer is selected from the group consisting of acrylic acid, methacrylic acid, acrylamide and methacrylamide.

6. The process of claim 4 in which said mixture of monomers comprises from about 10 to about 80% by weight of said first monomer, from about 5 to about 35% by weight of an acid comonomer selected from the group consisting of acrylic and methacrylic acids and from about 10 to about 85% by weight of an amide comonomer selected from the group consisting of acrylamide and methacrylamide.

7. The process of claim 1 in which said cross-linking agent is selected from the group consisting of the compounds defined by structural formulas I, II and III below:

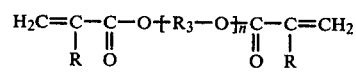

wherein R is hydrogen or $C_1$ to $C_4$ alkyl; $R_3$ is $C_1$ to $C_6$ alkylene; and n is an integer from 1 to 3;

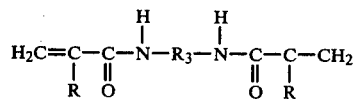

wherein R is hydrogen or $C_1$ to $C_4$ alkyl; and $R_3$ is $C_1$ to $C_6$ alkylene; and

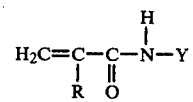

wherein R is hydrogen or $C_1$ to $C_4$ alkyl; and Y is selected from the group consisting of

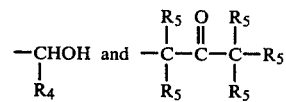

wherein $R_4$ is selected from the group consisting of hydrogen and $C_1$ to $C_5$ alkyl; and each $R_5$ is selected from the group consisting of hydrogen and $-CH_2OH$, provided, however, that at least one $R_5$ is $-CH_2OH$.

8. The process of claim 6 in which said crosslinking agent is N,N'-methylenebisacrylamide, and is present in an amount of from about 0.05 to about 1% by weight, based on the weight of the monomer mixture.

9. The process of claim 1 in which said water miscible solvent is methanol.

10. The process of claim 1 in which the free radical initiator is a chemical initiator.

11. The process of claim 10 in which said chemical initiator comprises ammonium persulfate.

12. The process of claim 11 in which the ammonium persulfate content is from about 0.5 to about 1% by weight based on the weight of the monomer mixture.

13. The process of claim 11 in which the polymerization is carried out at a temperature of from about 55° C. to about 75° C.